United States Patent [19]
Lagergren

[11] 3,935,864
[45] Feb. 3, 1976

[54] ENDOCARDIAL ELECTRODE

[76] Inventor: Hans Lagergren, Ostermalmsgatan 89, S11459, Stockholm, Sweden

[22] Filed: June 18, 1974

[21] Appl. No.: 480,536

[30] Foreign Application Priority Data
July 4, 1973   Germany.......................... 2334049

[52] U.S. Cl. ............................. 128/418; 128/419 P
[51] Int. Cl.². ........................................ A61N 1/04
[58] Field of Search ........... 128/404, 416, 417, 418, 128/419 P

[56] References Cited
UNITED STATES PATENTS

| | | | |
|---|---|---|---|
| 1,480,353 | 1/1924 | Wappler | 128/417 |
| 3,485,247 | 12/1969 | Ackerman | 128/418 |
| 3,749,101 | 7/1973 | Williamson | 128/418 |
| 3,760,812 | 9/1973 | Timm | 128/418 |
| 3,788,329 | 1/1974 | Friedman | 128/418 |
| 3,815,611 | 6/1974 | Benniston | 128/419 P |

Primary Examiner—William E. Kamm
Attorney, Agent, or Firm—Haseltine, Lake & Waters

[57] ABSTRACT

An endocardial electrode for effecting the intracardial stimulation of a heart, consisting of an elongated electrical conductor, which is provided with an electrical insulation, and an electrode head located at the distal end of the conductor which is proximate the heart, for the transmission of stimulative impulses to the heart through the applied electrode. The electrode head includes electrically conductive small-surfaced contact portions which are connected with the electrical conductor, and in which the individual contact portions are so constructed and arranged so as to form the edges of at least one hollow body or, respectively, a depression.

20 Claims, 7 Drawing Figures

ENDOCARDIAL ELECTRODE

FIELD OF THE INVENTION

The present invention relates to an endocardial electrode for effecting the intracardial stimulation of a heart, consisting of an elongated electrical conductor, which is provided with an electrical insulation, and an electrode head located at the distal end of the conductor which is proximate the heart, for the transmission of stimulative impulses to the heart through the applied electrode.

DISCUSSION OF THE PRIOR ART

In known endocardial electrodes of the above-mentioned type, the electrode head consists of a small metal cylinder connected at one end thereof to the electrical conductor, and which is rounded off at its other free end. This metal cylinder inherently forms the electrode, which imparts the electrical energy impulses of an impulse generator such as, for example, a pace maker, to the heart muscle for stimulation of the latter.

The energy of the impulses should, on the one hand, be as small as possible so that, for an implanted pace maker, the energy of the implanted batteries are not too rapidly used up; whereas, on the other hand, the impulse energy must be sufficiently large whereby each impulse assuredly effects the stimulation of the heart. In order to achieve this assurance, the impulse energy at the expense of the service life of the batteries has, however, been selected so as to be relatively highly, whereby even for a high stimulative threshold for the heart, the stimulating energy of the impulses is sufficiently large. In connection with the foregoing, it must be considered that the stimulative threshold of the heart does not remain constant for any length of time, and mostly increases after implanation. The setting of the impulse energy to a minimum value which is determined upon implantation — so as to increase the service life of the batteries — has fatal results for the patients upon an increase in the stimulative threshold.

SUMMARY OF THE INVENTION

In view of the foregoing situation, it is an object of the present invention to provide an endocardial electrode of the above-mentioned type, which allows for the use thereof at a low impulse energy, without jeopardizing the safety of the patients. The invention utilizes the basic premise that the raising in the stimulative threshold of the heart after implantation is a result in that between the electrode and the muscle tissue which are stimulated, scar tissue is formed, and/or cellular and connecting tissue sections. This causes the raising away of the electrode from the stimulable muscle, in view of which there is a reduction in the current density at the muscle which is responsible for effecting the stimulation.

The practical object which is derived from the foregoing knowledge is applied to the present invention in that the electrode is so constructed, whereby notwithstanding the low energy level of the individual impulses sufficiently high current densities is generated, which are transmitted to the stimulable cells of the heart muscle. The foregoing is inventively attained is that the electrode head includes electrically conductive small-surfaced contact portions which are connected with the electrical conductor, and in which the individual contact portions are so constructed and arranged as to form the edges of at least one hollow body or, respectively, a depression. Preferably, the surface of the contact portions are not larger than 15 mm$^2$, and suitably consist of 2 mm$^2$. It is particularly advantageous when the electrode head is formed of a coarse-meshed basket, in which the surface of the meshes is approximately 3 mm$^2$ in average. The base of the basket thereby forms the outermost or distal end of electrode head, and the basket opening is closed off through the conductor insulation. In a particularly preferred embodiment of the invention, in order to increase the weight of the electrode head, centrally of the interior of the basket there is positioned a weight, which preferably is in the form of a rod.

BRIEF DESCRIPTION OF THE DRAWING

Further advantages and embodiments of the invention may be ascertained from the following detailed description, taken in conjunction with the accompanying drawing, in which.

DETAILED DESCRIPTION

Figure 1:
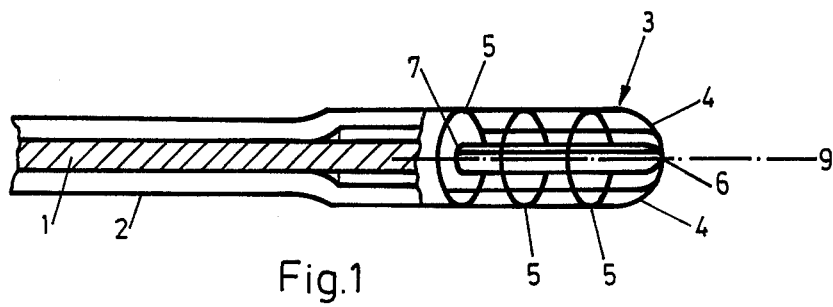
FIG. 1 illustrates the distal implantable end of an endocardial electrode having a basket-shaped electrode head.

Referring now in detail to the drawing, FIG. 1 illustrates an elongate electrical conductor 1 of an electrode, which is provided with an electrical insulation 2. At the distal end of the electrode there is located an electrode head 3 connected at one end thereof to the electrical conductor. The electrode head is essentially cylindrically-shaped and is rounded off at its free end. As shown in FIG. 1, electrode head 3 is formed of longitudinally extending wire loops 4 which are transversely stiffened by means of circularly bent wire loops 5. In order to stabilize the basket-forming wire mesh constituted by loops 4 and 5, and in order to increase the weight of the electrode head, a metal rod 6 is centrally located within the wire basket which forms the electrode head. At its rearmost end 7, the rod 6 is connected with the elongate electrical conductor 1. The basket-forming wire mesh constituted by the longitudinal wire loops 4 and the circular stiffening wire loops 5 affords the electrode, after application in the heart to provide space for the tissue being formed so as to prevent raising away of the electrode from the stimulable heart muscle.

In lieu of the wire loops 4 and 5 forming a cylindrical wire-mesh basket structure, generally flat bands of metal or electrically conductive material may be employed. The bands are intertwined in a suitable manner to form the basket-like configuration as shown in FIG. 1. The band material may be of a width in the range of 0.01 to 1.0 mm, and preferably of about 0.2 mm.

Figure 2A:
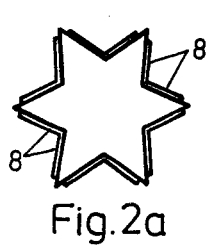
FIG. 2a is a transverse section through the electrode head of FIG. 2 on an enlarged scale.
Figure 2:
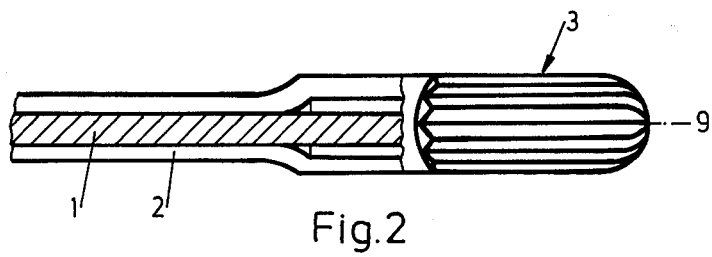
FIG. 2 shows a second electrode head having a star-like cross-sectional configuration.
Figure 3A:
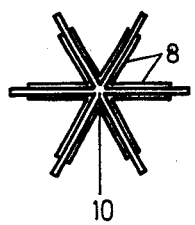
FIG. 3a is a transverse section through the electrode head of FIG. 3 on an enlarged scale.
Figure 3:
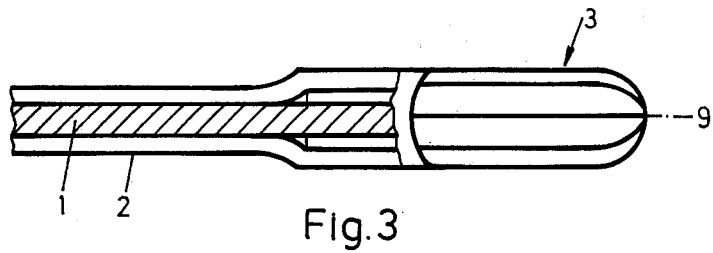
FIG. 3 shows a third embodiment of an electrode head having a star-like cross-sectional configuration.

The cylindrical star-shaped electrode head 3 shown in FIGS. 2 and 2a of the drawing is constructed of metal and is covered with an insulating material 8 to an extent in which only the edges of the star-shaped depressions are not insulated. The insulating surfaces are located between the projecting electrically conductive edges of the star-shaped depressions (recesses or, respectively, hollow spaces) which again provides for the ability of receiving tissue which is expected to grow after implantation. The depression may, in accordance with FIGS. 3 and 3a, be enlarged so as to form a star-shaped cross-section, such as may be encountered in an ice crystal. In the embodiment of FIGS. 2 and 3 it is also possible that, in lieu of the insulative covering 8, the entire electrode head is constructed of insulating material and merely the outer edges are provided with electrically conductive portions. In the instance of the embodiment of FIG. 3a, along the symmetrical axis (which is designated in all of the figures with the reference numeral 9) of the electrode head, there is positioned a metal body 10 which corresponds with rod 6 in FIG. 1.

Figure 4A:
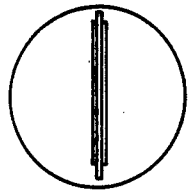
FIG. 4a is a transverse section through FIG. 4 on an enlarged scale.
Figure 4:
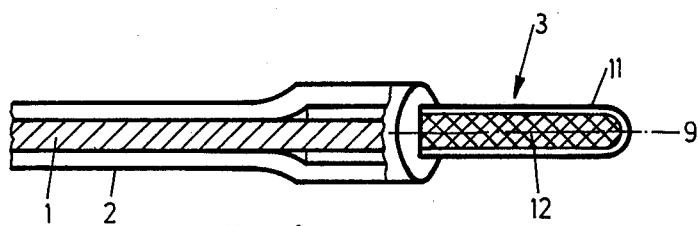
FIG. 4 illustrates an electrode head having a wire loop.

In the embodiment of FIG. 4, the electrode head 3 consists of a wire or, respectively, a band loop 11, wherein the space encompassed by this loop may be filled with an insulating material 12. In this embodiment, after implantation, the tissue being formed may grow along the wide surfaces of the tongue-like shaped electrode head, while the edges formed by the band-like wire material further remain in close contact with the stimulable heart muscle.

The contact portions 4, 5, in comparison with known cylindrical electrode heads, have a small surface and in their illustrated arrangement and construction define the outer edges of hollow bodies or depressions, comparing in particular the embodiment of FIGS. 1 through 3.

While there has been shown what is considered to be the preferred embodiment of the invention, it will be obvious that modifications may be made which come within the scope of the disclosure of the specification.

What is claimed is:

1. Endocardial electrode for the intracardial stimulation of a heart, comprising an elongate electrical conductor; and electrical insulation encasing said conductor; and an electrode head being connected to said conductor at the end thereof proximate the heart for transmission of stimulative pulse to the heart upon insertion of said electrode, said electrode head having a plurality of electrically conductive contact portions connected to said conductor and defining spaces extending interiorly of said electrode head, said contact portions being shaped and positioned so as to form the external periphery-defining edges of at least one hollow body in said electrode head.

2. Endocardial electrode as claimed in claim 1, said hollow body being a depression in said electrode head.

3. Endocardial electrode as claimed in claim 1, said contact portions having a collective surface area of up to 15 mm².

4. Endocardial electrode as claimed in claim 3, said surface area being about 2 mm².

5. Endocardial electrode as claimed in claim 1, said electrode head comprising an essentially cylindrical coarse-meshed wire basket.

6. Endocardial electrode as claimed in claim 5, said mesh having an encompassed area in the range of about 2 to 5 mm².

7. Endocardial electrode as claimed in claim 5, said electrode head having the outermost end formed by the base of said wire basket, and an elongate electrical conductor being connected to the opening of said basket so as to close the latter.

8. Endocardial electrode as claimed in claim 5, comprising weight means being positioned interiorly of said electrode head for increasing the weight thereof.

9. Endocardial electrode as claimed in claim 8, said weight means comprising a rod extending centrally and axially of said wire basket.

10. Endocardial electrode as claimed in claim 1, each said contact portion being formed of electrically conductive wire material.

11. Endocardial electrode as claimed in claim 1, each said contact portion being formed of electrically conductive band material.

12. Endocardial electrode as claimed in claim 1, said electrode head being substantially cylindrical and star-shaped in transverse section.

13. Endocardial electrode as claimed in claim 12, the outer longitudinally extending edges of said star-shaped cylindrical electrode head comprising said electrically conductive contact portions.

14. Endocardial electrode as claimed in claim 13, said contact portions comprising the outer edges of said hollow body so as to define the outer contour of said electrode head.

15. Endocardial electrode as claimed in claim 1, said electrode head being essentially formed of a material having a high specific weight.

16. Endocardial electrode as claimed in claim 1, said contact portions being a band material in an intertwined configuration forming an essentially cylindrical basket-like electrode head.

17. Endocardial electrode as claimed in claim 16, said band material having a width in the range of about 0.01 to 1.0 mm.

18. Endocardial electrode as claimed in claim 17, said band material having a width of 0.2 mm.

19. Endocardial electrode as claimed in claim 13, the interstitial hollows between the outer longitudinally extending edges being formed of electrically insulating material.

20. Endocardial electrode as claimed in claim 13, the interstitial hollows between the outer longitudinally extending edges being formed of insulated electrically conductive material.

* * * * *

REEXAMINATION CERTIFICATE (942nd)

United States Patent [19]

Lagergren

[11] B1 3,935,864
[45] Certificate Issued Nov. 8, 1988

[54] ENDOCARDIAL ELECTRODE

[76] Inventor: Hans Lagergren, Ostermalmsgatan 89, S11459, Stockholm, Sweden

Reexamination Request:
No. 90/000,914, Nov. 27, 1985

Reexamination Certificate for:
Patent No.: 3,935,864
Issued: Jun. 18, 1974
Appl. No.: 480,536
Filed: Feb. 3, 1976

[30] Foreign Application Priority Data

Jul. 4, 1973 [DE] Fed. Rep. of Germany ....... 2334049

[51] Int. Cl.$^4$ ................................................ A61N 1/04
[52] U.S. Cl. .................................. 128/786; 128/419 P
[58] Field of Search ...................... 128/419 P, 784, 786

[56] References Cited

U.S. PATENT DOCUMENTS

| | | |
|---|---|---|
| 164,184 | 6/1875 | Kidder . |
| 623,022 | 4/1899 | Johnson . |
| 932,775 | 8/1909 | Gaston . |
| 1,480,353 | 1/1924 | Wappler . |
| 1,889,271 | 11/1932 | Zerne . |
| 2,536,271 | 1/1951 | Fransen . |
| 2,854,983 | 10/1958 | Baskin . |
| 3,216,424 | 11/1965 | Chardack . |
| 3,367,339 | 10/1964 | Sessions . |
| 3,397,699 | 8/1968 | Kohl . |
| 3,403,684 | 12/1970 | Stiebel . |
| 3,472,234 | 10/1969 | Tachick . |
| 3,516,410 | 6/1970 | Hakim . |
| 3,543,761 | 12/1970 | Bradley . |
| 3,721,246 | 3/1973 | Landis . |
| 3,724,467 | 4/1973 | Avery . |
| 3,737,579 | 6/1973 | Bolduc . |
| 3,738,368 | 6/1973 | Avery . |
| 3,749,101 | 7/1973 | Williamson ........................ 128/786 |
| 3,750,650 | 8/1973 | Ruttgers . |
| 3,760,812 | 9/1973 | Timm . |
| 3,814,104 | 6/1974 | Irnich . |
| 3,817,252 | 6/1974 | Maurer . |

FOREIGN PATENT DOCUMENTS

| | | |
|---|---|---|
| 6940435 | 10/1969 | Fed. Rep. of Germany . |
| 1514356 | 12/1969 | Fed. Rep. of Germany . |
| 2060727 | 6/1971 | France . |
| 2180908 | 4/1973 | France . |
| 7203411 | 5/1973 | Netherlands . |
| 7305358 | 10/1973 | Netherlands . |
| 7305359 | 10/1973 | Netherlands . |
| 1219017 | 1/1971 | United Kingdom . |
| 1242550 | 8/1971 | United Kingdom . |
| 1236075 | 8/1972 | United Kingdom . |
| 1313486 | 4/1973 | United Kingdom . |
| 1316072 | 5/1973 | United Kingdom . |
| 1315964 | 5/1973 | United Kingdom . |

OTHER PUBLICATIONS

Post-Operative Variations in the Electrophysiology of the Epicardial Onlay Pacemaker Lead, Nicholas P. D. Smyth, M.D. et al, Medical Annals of the District of Columbia, vol. 40, No. 1, Jan. 1971, pp. 12-15.

"An Implantable Synchronous Pacemaker for the Long Term Correction of Complete Heart Block", by David A. Nathan, M.D., et al, published in The American Journal of Cardiology, pp. 362-367, Mar. 1963.

"Endocardial Electrical Threshold of Human Cardiac Response as a Function of Electrode Surface Area", by S. Furman, et al, published in the Digest of the 7th International Conference on Medical and Biological Engineering, 1967, Stockholm.

"Electrodes for Cardiac Pacing", by Hans Lagergren, et al, published in: Cardiac Pacing Proceedings of the 4th Intl. Symposium on Cardiac Pacing, Groningen, 1975, pp. 235-238.

Furman et al, "Journal of Surgical Research, Clinical & Laboratory Investigation, vol. 11, No. 3, Mar. '71, pp. 105-110.

Clark Leland C. et al.-"Bioelectrodes for Tissue Metabolism" Annals of the N.Y. Academy of Sciences, vol. 148-Art. I-pp. 133-153 (Feb. 1, 1968).

Deutsch, Sid-"A Probe to Monitor Electroanesthesia Current Density", IEEE Transactions on Bio-Medical Engineering, vol. 15-pp. 130-131 (Apr., 1968).

Guyton, David L. et al.-"Theory and Design of Capacitor Electrodes for Chronic Stimulation", Medical and Biological Engineering, pp. 613-619 (Sep., 1974).

Hassler, C. R. et al-"The Effects of Electrode Configuration and Calculated Current Density Upon Electrically Augmented Bone Healing in Rabbit Calvaria", Proceeding of the 27th Annual Conference on Engineering in Medicine and Biology, vol. 16-p. 297-(Oct. 6-10, 1974).

Kahn, A.-"Motion Artifacts and Streaming Potentials in Relation to Biological Electrodes", Digest of 6th International Conference on Medical Electronics & Biological Engineering-1965-Tokyo, 33-3 (two pages unnumbered).

Pollak, V.-"The Waveshape of Action Potentials Recorded with Different Types of Electromyographic Needles", Bio-Medical Engineering, Electrical Engineering Dept.-pp. 657-663 (Apr., 1971).

(List continued on next page)

*Primary Examiner*—William E. Kamm

[57] ABSTRACT

An endocardial electrode for effecting the intracardial stimulation of a heart, consisting of an elongated electrical conductor, which is provided with an electrical insulation, and an electrode head located at the distal end of the conductor which is proximate the heart, for the transmission of stimulative impulses to the heart through the applied electrode. The electrode head includes electrically conductive small-surfaced contact portions which are connected with the electrical conductor, and in which the individual contact portions are so constructed and arranged so as to form the edges of at least one hollow body or, respectively, a depression.

OTHER PUBLICATIONS

Rositano, Salvatore A. et al.-"Ultraflexible Bioelectrodes and Wires", Proceedings of the 23rd Annual Conference on Engineering in Medicine and Biology-Washington, D.C., p. 149-(Nov. 15-19, 1970).

Schaudinischky, L. et al.-"New Method of Measurement of Bioelectric Potentials", Proceedings of the 21st Annual Conference on Engineering in Medicine and Biology-Houston, Texas, p. 13 A3 (Nov. 18-21, 1968).

Schaudinischky, L.-"Technical Note-The Shape Conforming Electrode Medical and Biological Engineering, vol. 7-pp. 341-343 (Pergamon Press, 1969).

Stone, T. W.-"A Bipolar Electrode for Localized Directional Stimulation", Experientia, vol. 13, No. 6-pp. 666-667 (1973).

Timm, Gerald W. et al.-"Electromechanical Restoration of the Micturition Reflex, IEEE Transactions on Bio-Medical Engineering, vol. BME-18-No. 4-pp. 274-280, (Jul., 1971).

Berens, Stephen C., M.D. et al.-"New Stable Temporary Atrial Pacing Loop", The American Journal of Cardiology, vol. 34-No. 3-pp. 325-332 (Sep., 1974).

Thalen, H. J. TH., M.D.-"The Artificial Cardiac Pacemaker, Its History, Development and Clinical Application", pp. 145-161 (1969) Published by Charles C. Thomas.

Beard, Richard B. et al, "Porous Cathodes for Implantable Hybrid Cells", IEEE Transactions on Biomedical Engineering, vol. BME-19-No. 3-pp. 233-238 (May, 1972).

Smyth, Nicholas, P.D., et al-"An Epicardial Synchronous Pacemaker Lead ", The Annals of Thoracic Surgery, vol. 3-No. 2-pp. 119-125 (Feb., 1967).

Galante, Jorge, M.D. et al-"Sintered Fiber Metal Composites as a Basis for Attachment of Implants to Bone", The Journal of Bone and Joint Surgery, vol. 53-A-No. 1-pp. 101-114 (Jan., 1971).

Hulbert, S. F. et al.-"Tissue Reaction to Three Ceramics of Porous and Non-Porous Structures", Biomed. Mater. Res., vol. 6-pp. 347-351 (1972).

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

The patentability of claims 4–20 is confirmed.

Claims 1–3 are cancelled.

* * * * *